(12) United States Patent
Tata

(10) Patent No.: US 8,383,046 B1
(45) Date of Patent: Feb. 26, 2013

(54) ANALYZER APPARATUS FOR MEASURING DISSOLVED VOLATILE SUBSTANCES AND METHOD

(76) Inventor: Murthy Tata, Chandler, AZ (US)

( * ) Notice: Subject to any disclaimer, the term of this patent is extended or adjusted under 35 U.S.C. 154(b) by 1167 days.

(21) Appl. No.: 12/103,468

(22) Filed: Apr. 15, 2008

Related U.S. Application Data

(60) Provisional application No. 60/923,645, filed on Apr. 16, 2007.

(51) Int. Cl.
*G01N 21/17* (2006.01)
(52) U.S. Cl. ............... 422/82.05; 422/82.07; 422/82.08
(58) Field of Classification Search ....... 422/68.1–82.13
See application file for complete search history.

(56) References Cited

U.S. PATENT DOCUMENTS

| | | | |
|---|---|---|---|
| 4,892,383 A * | 1/1990 | Klainer et al. .................. 385/12 |
| 5,000,919 A * | 3/1991 | Heckmann .................... 422/401 |
| 5,116,759 A * | 5/1992 | Klainer et al. ............. 435/287.2 |
| 5,144,831 A | 9/1992 | Hale et al. |
| 5,514,253 A * | 5/1996 | Davis et al. ................... 422/68.1 |
| 6,138,497 A | 10/2000 | Nix et al. |
| 6,192,737 B1 * | 2/2001 | Ohlrogge et al. ............ 73/19.06 |
| 6,874,351 B2 * | 4/2005 | Bloder et al. ................ 73/19.05 |
| 2003/0177814 A1 * | 9/2003 | Weckstrom et al. ......... 73/25.01 |
| 2006/0255301 A1 * | 11/2006 | Nortier et al. ............ 251/129.03 |

FOREIGN PATENT DOCUMENTS

| | | |
|---|---|---|
| EP | 0103988 | 3/1984 |
| EP | 0429397 | 5/1991 |

* cited by examiner

*Primary Examiner* — Jill Warden
(74) *Attorney, Agent, or Firm* — Parsons & Goltry; Robert A. Parsons; Michael W. Goltry

(57) ABSTRACT

Analyzer apparatus for measuring amounts of a specific analyte dissolved in a liquid includes a measurement cavity block defining a measurement cavity and an analyte inlet in communication with the measurement cavity, an analyte sensor assembly selected to sense the specific analyte being affixed to the block in communication with the measurement cavity and sealing the measurement cavity from environment outside the measurement cavity, and a semipermeable membrane affixed to the measurement cavity block over the analyte inlet with the measurement cavity being sealed from environment outside the measurement cavity except for analyte entering the measurement cavity through the semipermeable membrane.

14 Claims, 7 Drawing Sheets

ANALYZER APPARATUS FOR MEASURING DISSOLVED VOLATILE SUBSTANCES AND METHOD

CROSS-REFERENCE TO RELATED APPLICATIONS

This application claims the benefit of U.S. Provisional Application No. 60/923,645, filed 16 Apr. 2007.

FIELD OF THE INVENTION

This invention generally relates to analyzer apparatus and methods of measuring the amounts of dissolved volatile substances in a liquid.

BACKGROUND OF THE INVENTION

There is a need to quickly measure the amounts of volatile species (hereinafter referred to as an analyte or analytes) dissolved in a liquid. Some examples include the measurement of dissolved carbon dioxide in water, beer, soda, wines, blood, and natural bodies of water such as in lakes, streams and marine systems. Other examples include measurement of flavors, ammonia, alcohol, etc. in various aqueous systems, or simply to measure vapor pressures of pure liquids.

One type of prior art device used to measure the amount of alcohol in liquids uses a sensor probe that is submersed in the liquid to be tested and includes a permeable membrane that allows the volatile alcohol to permeate through while blocking the water. The gaseous alcohol that permeates through the membrane is carried by a gas carrier in a measurement gas space through pairs of infrared sensors in a continuous flow. The sensors measure the concentration of alcohol in the liquid. This type of device is shown and explained in U.S. Pat. No. 6,834,536, entitled "Probe for Measuring Alcohol in Liquids", issued 28 Dec. 2004.

By definition, (Ref. pp. 17-14, Perry's Handbook of Chemical Engineers, $6^{th}$ ed., R. H. Perry and D. Green (eds)., 1984, McGraw Hill) molecules of the volatile substance have to first dissolve in the membrane on the liquid-side, then diffuse through the membrane, and desorb into the gas phase where the sensor is located. Such a permeation process can be agonizingly slow, and may be affected by the presence of other components present in solution.

The gas carrier must be provided for the device to operate with a reasonably small time constant, in which case, the small amounts of alcohol permeating will be diluted significantly making it harder for accurate sensing. This type of device is specifically designed for liquids with high alcohol concentrations that cannot be accurately measured with solid-state detectors. Further, because of the type of membrane used and the size of the measurement gas space, only high alcohol concentrations can be measured.

It would be highly advantageous, therefore, to remedy the foregoing and other deficiencies inherent in the prior art.

Accordingly, it is an object of the present invention to provide new and improved analyzer apparatus for measuring the amounts of dissolved volatile substances in a liquid.

It is another object of the present invention to provide a new and improved method for measuring the amounts of dissolved volatile substances in a liquid.

SUMMARY OF THE INVENTION

Briefly, to achieve the desired objects of the instant invention in accordance with a preferred embodiment thereof, analyzer apparatus for measuring amounts of at least one specific analyte dissolved in a liquid includes a measurement cavity block defining a measurement cavity and an analyte inlet in communication with the measurement cavity. An analyte sensor assembly is selected to sense the at least one specific analyte and is sealingly affixed to the block with the analyte sensor assembly in communication with the measurement cavity, the sensor assembly sealing the measurement cavity from environment outside the measurement cavity. A semipermeable membrane is affixed to the measurement cavity block over the analyte inlet with the measurement cavity sealed from environment outside the measurement cavity except for the analyte entering the measurement cavity through the semipermeable membrane.

The desired objects of the instant invention are further realized in accordance with a specific embodiment in which a method of measuring amounts of a specific analyte dissolved in a liquid comprises the following steps. Analyzer apparatus is provided that includes a measurement cavity block defining a measurement cavity and an analyte inlet in communication with the measurement cavity, an analyte sensor assembly selected to sense the specific analyte, a sensor mounting plate having the analyte sensor assembly mounted thereon, the sensor mounting plate being affixed to the block with the analyte sensor assembly in communication with the measurement cavity, and the sensor mounting plate sealing the measurement cavity from environment outside the measurement cavity, and a semipermeable membrane affixed to the measurement cavity block over the analyte inlet with the measurement cavity being sealed from environment outside the measurement cavity except for analyte entering the measurement cavity through the semipermeable membrane. Using the provided analyzer apparatus a sample liquid, including a specific analyte dissolved therein, is brought into communication with the semipermeable membrane and analyte is allowed to flow into the measurement cavity. The analyte sensor assembly is activated to provide a measurement of the analyte in the measurement chamber and the concentration of analyte in the sample is determined.

In a specific embodiment of the method the concentration of analyte in the sample is determined by either using thermodynamic vapor-liquid equilibrium relationships, estimating the corresponding concentration of analyte dissolved in the liquid from the measured amount of analyte in the measurement cavity or using the analyte amount measured in the measurement cavity directly as a measure of the corresponding concentration in the liquid.

The desired objects of the instant invention are further realized in accordance with a specific embodiment of another method of measuring amounts of a specific analyte dissolved in liquid. This method includes the steps of providing an analyzer block containing a measurement cavity, at least one analyte sensor responding to the amount of analyte accumulating in the measurement cavity, and a pathway for gas communication from the measurement cavity for sample presentation. No membrane is used in this structure. A container of liquid containing a dissolved analyte is provided in which the container defines a headspace free of the liquid. The headspace of the container is connected to the gas communication pathway so that the headspace of the container is in communication with the measurement cavity and the analyte is allowed to diffuse from the liquid into the gas communication pathway and into the measurement cavity. The analyte sensor is activated to provide a measurement of the analyte in the measurement chamber and the concentration of the analyte in the liquid sample is determined from the measurement.

BRIEF DESCRIPTION OF THE DRAWINGS

The foregoing and further and more specific objects and advantages of the instant invention will become readily apparent to those skilled in the art from the following detailed description of a preferred embodiment thereof taken in conjunction with the drawings, in which.

DETAILED DESCRIPTION OF THE DRAWINGS

Figure 1:
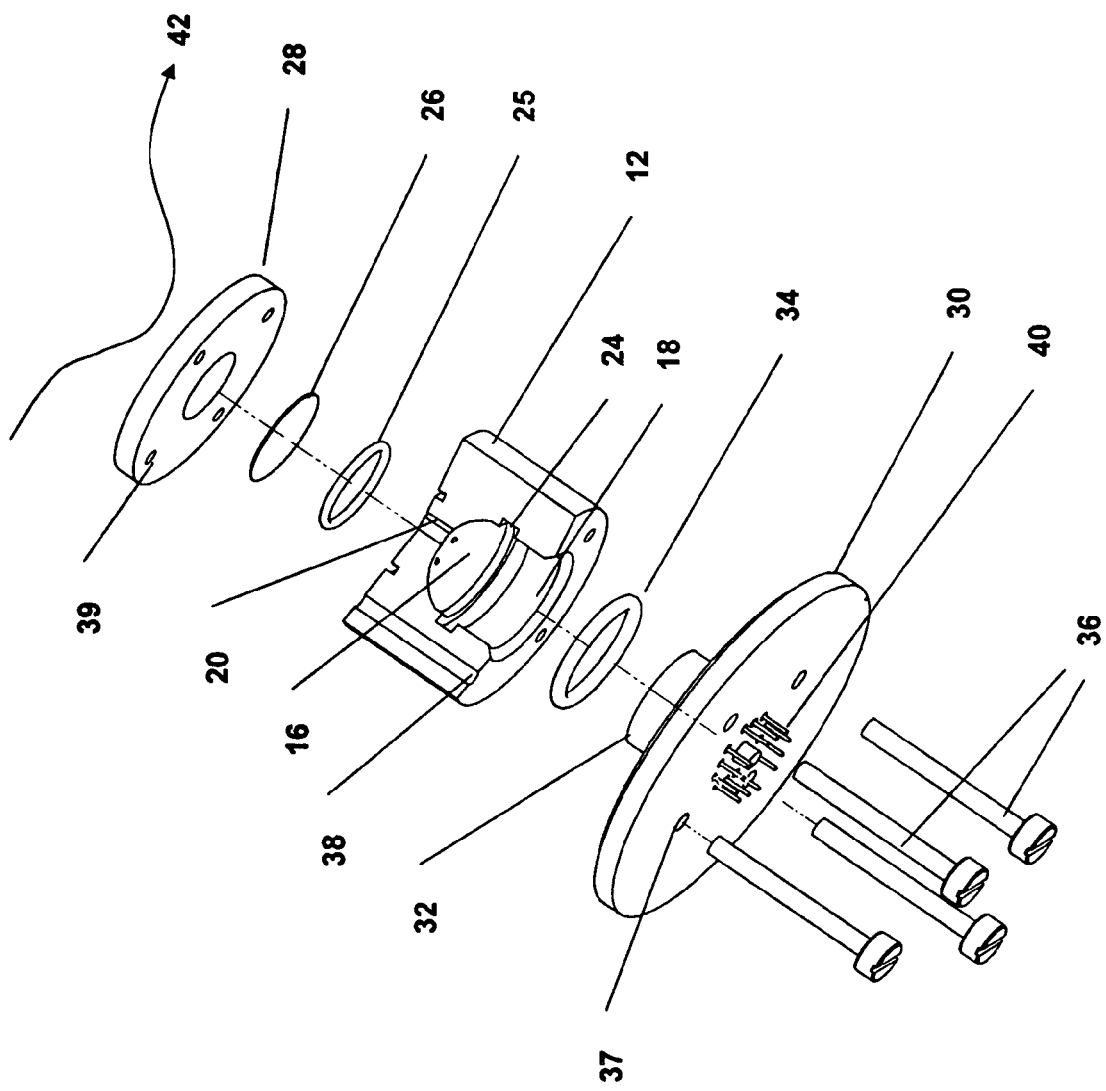
FIG. 1 is an exploded view in perspective, portions thereof cut away, of analyzer apparatus, in accordance with the present invention.

The present invention pertains to a dissolved volatile substances analyzer that uses a semi-permeable membrane that is analyte-permeable but substantially impervious to the liquid carrying the analyte. Generally, the membrane is set up as a separator between a small measurement cavity and the liquid-analyte solution or mixture. The measurement cavity is otherwise sealed to prevent leaking of the analyte to the outside environment. When the liquid-analyte solution or mixture passes over the membrane or is juxtaposed to the membrane, some of the analyte dissolved in the liquid pass through the membrane into the measurement cavity. Given sufficient time, the analyte accumulates in the measurement cavity until equilibrium is attained with the liquid sample. Based on the thermodynamic vapor-liquid equilibrium relationships, an estimate of the corresponding concentration of analyte dissolved in the liquid by measuring the amounts of analyte in the measurement cavity. Alternately, the analyte amount measured in the measurement cavity can itself be directly used as a measure of its corresponding concentration in the liquid.

In some applications, measuring the total pressure in the measurement cavity might be sufficient to estimate the analyte amounts (concentration) in the liquid. However, the total pressure may be a poor indicator of the analyte amount when there are multiple volatile substances, or when the liquid itself has a significant vapor pressure. For example, when measuring the amount of dissolved carbon dioxide when there is a finite amount of dissolved oxygen and nitrogen from air, using total pressure measurements cause a significant overestimation of the dissolved carbon dioxide concentration. A detector that is sensitive only to the analyte of interest will provide an accurate determination of the analyte quantities without interferences from other substances. Suitable detectors may vary with the specific analyte of interest. For example, when the analytes of interest include carbon dioxide or certain volatile organic compounds, a detector might assess the absorption of infrared radiation at the appropriate wavelengths. If measuring the concentration of electrochemically oxidizable or reducible analytes, an electrochemical detector might be more appropriate. If the analyte contains sulfur atoms, a sulfur chemiluminescence detector might be appropriate. If the analyte contains halogen groups, an electron-capture-efficiency detector might be more appropriate. In each application it is preferable to use an analyte sensor that is specific to the type of analyte being sensed.

For maximum sensitivity and speed of response, it is preferable to employ a membrane with high permeability for the analyte of interest. Since highly permeable membranes allow rapid equilibrium between the measurement cavity and the liquid sample, they also minimize the risk of condensation of vapor within the measurement cavity. Among the membranes with high permeability characteristics, it is preferable to select membranes that exhibit a high diffusion rate and a low solubility for the analyte. Such a membrane exhibits a lower propensity to absorb the analyte, thus enabling a faster response time. Suitable membranes can be fashioned from materials such as silicone, polyolefin, polyamide, polysulfone, polytetrafluoroethylene, polyvinyledene difluoride, etc. Such membranes can be fabricated separately, or cast in situ by suitable techniques including but not limited to solution casting and coacervation.

Membranes containing a microporous structure are ideal in this application because they provide extremely high diffusion rates and can be specifically developed for a wide variety of analytes. These membranes are quite different from traditional permeation membranes in that the membrane itself does not play any role in controlling diffusion of the analyte. The liquid phase is in direct communication with the gas phase through the pores in the membrane. The membranes chosen for aqueous systems are typically hydrophobic, and water does not "wet" the membrane, i.e., the pores remain filled with gas. Thus the steps of the analyte dissolving in the membrane at the liquid-membrane interface, diffusing through the membrane thickness, and evaporating on the gas side are obviated. Diffusion rates in these membranes can approach to within one order of magnitude of diffusion rates in gas phase and thus they provide extremely high diffusion rates. Since the analyte solvation step is irrelevant for analyte migration, different analytes can simultaneously diffuse through the membrane irrespective of their solubilities in the membrane material. Thus the membranes do not significantly discriminate between various analytes in a mixed liquid stream.

However, once the membrane pores are filled with liquid, the membrane performance rapidly deteriorates, with diffusion rates now approaching those in liquids, which are still 1-3 orders of magnitude faster than in solids. Only enormous pressures in the liquid phase can overcome these surface tension forces and force liquid to penetrate the pores and deteriorate the membrane performance. In most practical applications, with proper design, such pressures can be avoided to take advantage of these membranes.

Figure 2:
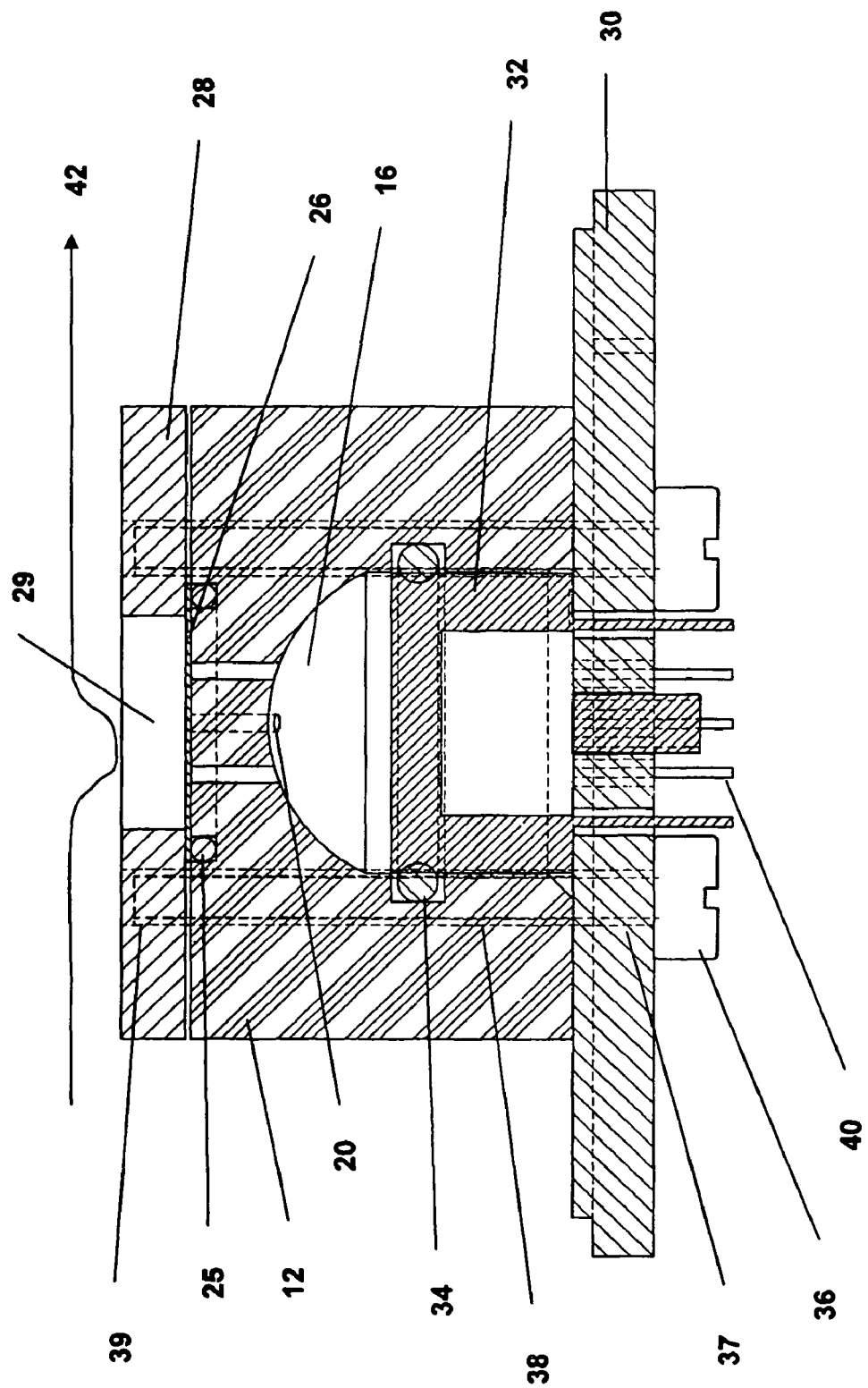
FIG. 2 is an enlarged cross-sectional view of the analyzer apparatus of FIG. 1.

Turning now to the drawings, attention is first directed to FIGS. 1 and 2 which illustrate one embodiment of analyzer apparatus, designated 10, in accordance with the present invention. Analyzer apparatus 10 includes a measurement cavity block 12, which in this embodiment is generally cylindrical in shape and defines a central cylindrical cavity 14. Cavity 14 has a generally dome shaped upper portion and, as will be explained presently, includes a measurement cavity 16 and a sensor receiving cavity 18. One or more axially extending fluid communication channels or holes 20 extend between the upper end of dome shaped measurement cavity 16 and the upper surface of block 12. In this specific embodiment an O-ring channel 22 is formed in the upper surface of block 12 extending circumferentially around fluid communication channels 20. Also, in this embodiment, an O-ring channel 24 extends around the periphery of cavity 14 between measurement cavity 16 and sensor receiving cavity 18.

An O-ring 25 is held in O-ring channel 22 and a semipermeable membrane 26, which as explained above preferably includes microporous structure, is positioned over the upper ends of fluid communication channels 20. A membrane retainer ring 28, having a central axially extending opening 29 therethrough, is positioned over membrane 26 with central opening 29 providing communication between fluid communication channels 20 and the exterior. Retainer ring 28 and O-ring 25 seals membrane 26 against the upper end of block 12 so that anything entering fluid communication channels 20 must pass through membrane 26. While an O-ring and mating channel are illustrated and described for convenience, it will be understood that any suitable sealing mechanism can be employed to secure and seal membrane 26 to measurement cavity block 12.

A detector mounting plate 30, which in this embodiment is generally disk shaped, has a suitable sensor assembly 32 mounted on the upper surface thereof. As will become clear from the description below, the various sensor assemblies described herein may contain one or more sensors. Plate 30 is formed to mate with the lower surface of block 12 and sensor assembly 32 is formed in a generally cylindrical shape to fit snuggly within sensor receiving cavity 18. An O-ring 34 is positioned in O-ring channel 24 in cavity 14 and engages the outer surface of sensor assembly 32 to seal measurement cavity 16 from the outside environment. While an O-ring and mating channel are illustrated and described for convenience, it will be understood that any suitable sealing mechanism can be employed to secure and seal sensor assembly 32 to measurement cavity block 12 and, thereby, to seal measurement cavity 16. The entire assembly is secured by using screws 36 that insert through holes 37 in detector mounting plate 30, through axially extending holes 38 in measurement cavity block 12, and thread into holes 39 in membrane retainer ring 28.

As explained above, sensor assembly 32 includes one or more suitable sensors selected for the specific analyte or analytes being measured and generates electrical or optical signals in response to the amounts of analyte sensed in measurement cavity 16. Sensor electrical or optical connections 40 extend from sensor assembly 32 through detector mounting plate 30 to provide external connections. It should be noted that in place of the O-rings described any other suitable sealing mechanisms and/or combinations thereof can be employed, for example adhesives, gaskets, etc. Also, to prevent stretching and deflection of the membrane, suitable mechanical supports, such as porous frits, fabrics, or even wire-mesh can be employed to buttress the membrane on either or both sides with due consideration to aspects of seal and integrity.

In operation, when a liquid, represented by arrow 42, flows past (or otherwise comes into contact with) membrane 26, any analytes in the liquid (i.e. a representative quantity) pass through membrane 26, through channels 20, and into measurement cavity 16 where sensor assembly 32 senses the amount of analyte and sends an electrical or optical signal through external leads (not shown) coupled to connections 40. As an example, when the analyte of interest is one that absorbs infrared radiation at specific wavelengths, a suitable sensor assembly 32 will include at least one infrared radiation source (e.g. a semiconductor diode or the like) and at least one infrared radiation detector (e.g. a semiconductor photosensor or the like) therein. Infrared radiation from the source will be projected onto the internal walls of measurement cavity 16, especially the opposing surface. The surfaces of measurement cavity 16 may be polished and coated with infrared radiation reflective material to improve sensitivity by minimizing absorption by the walls of measurement cavity 16. Alternately, a suitable infrared reflector may be incorporated within measurement cavity 16 to properly direct the radiation in cavity 16 from the source, through the gasses therein, and back into the detector element within sensor assembly 32.

Figure 3:
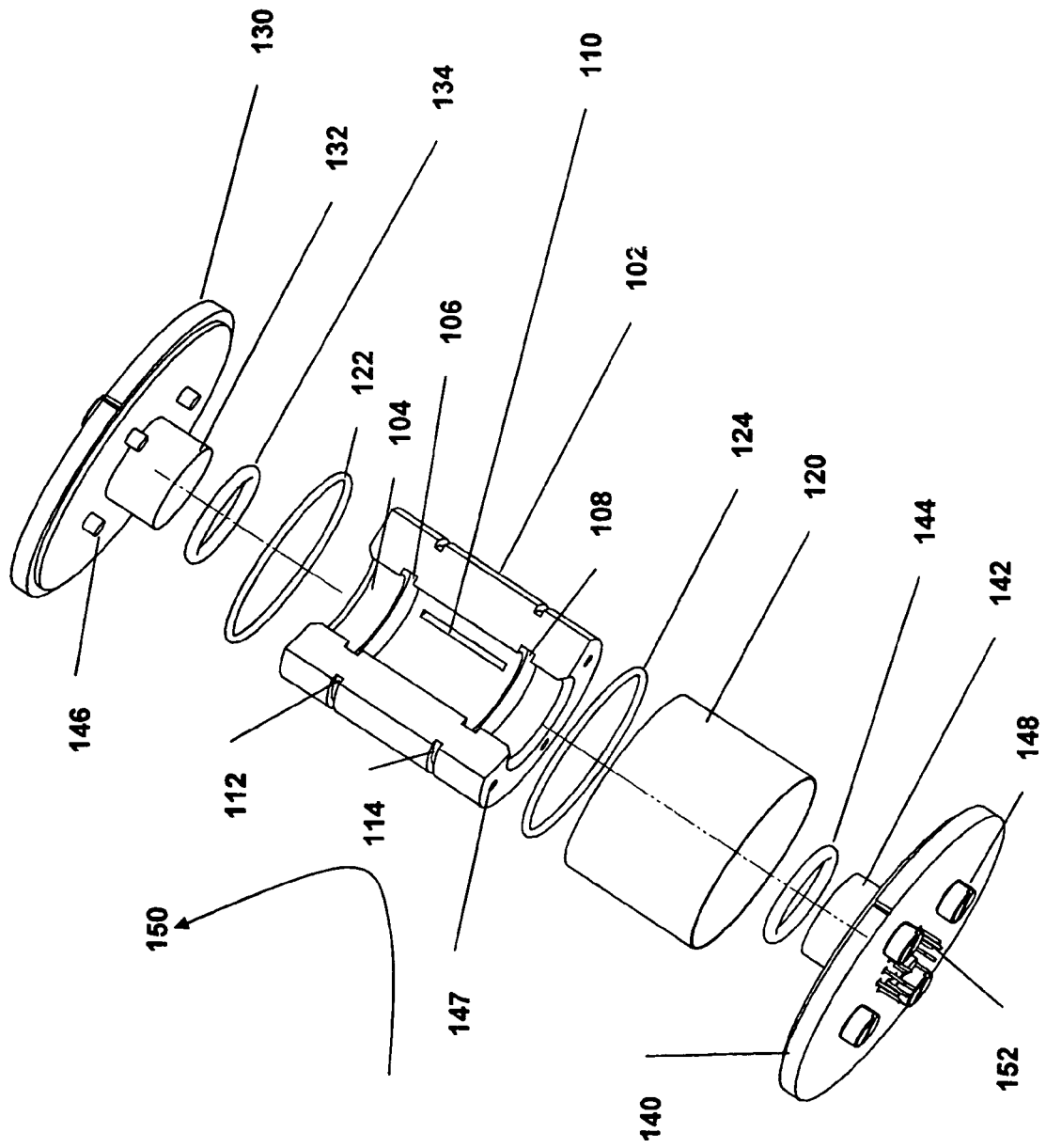
FIG. 3 is an exploded view in perspective, portions thereof cut away, of another embodiment of analyzer apparatus, in accordance with the present invention.
Figure 4:
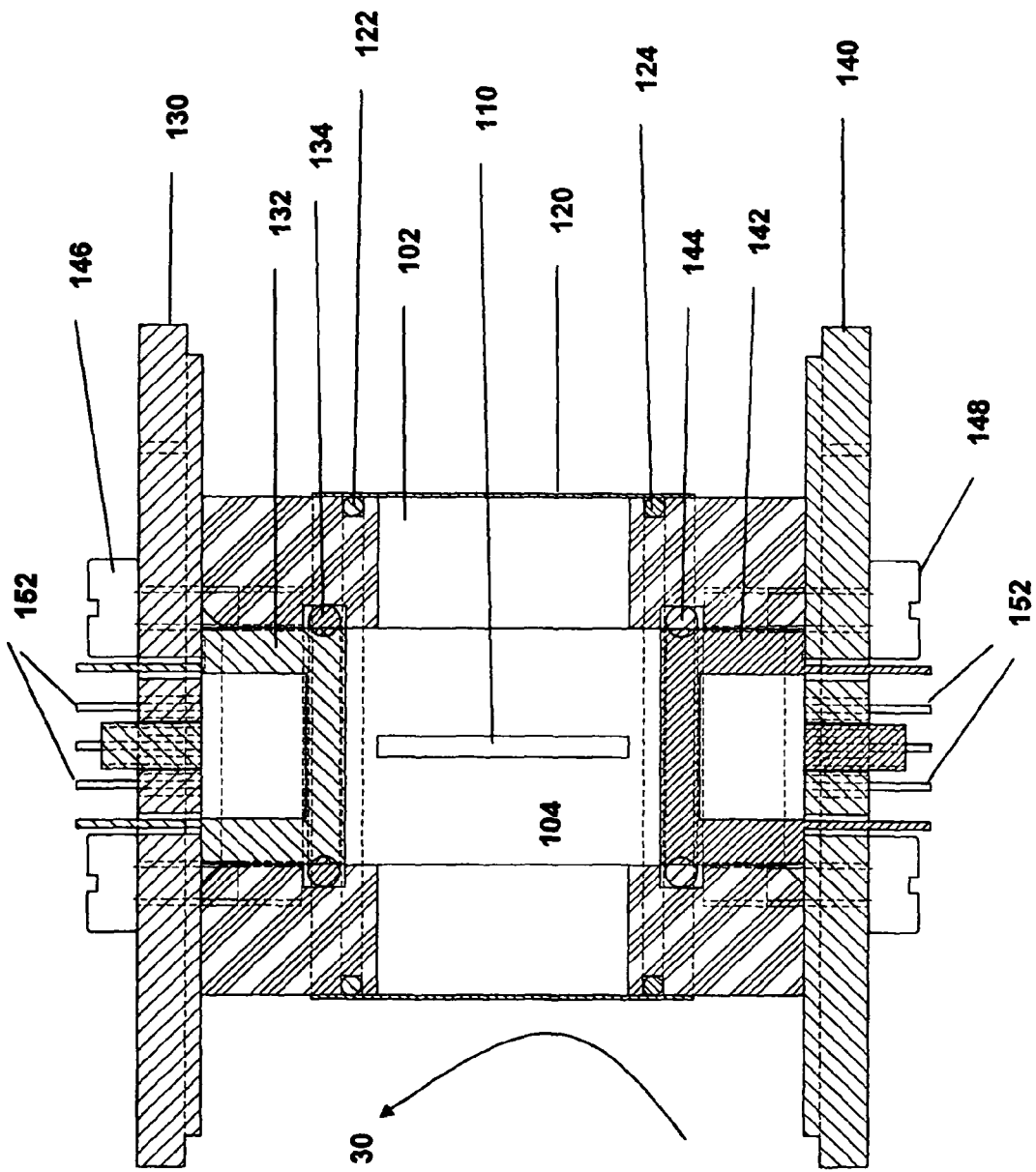
FIG. 4 is an enlarged cross-sectional view of the analyzer apparatus of FIG. 3.

Turning now to FIGS. 3 and 4, another embodiment of analyzer apparatus, designated 100, is illustrated in accordance with the present invention. Analyzer apparatus 100 includes a measurement cavity block 102, which in this embodiment is generally cylindrical in shape and defines a central cylindrical cavity 104 that extends axially through block 102. In this specific embodiment, an O-ring channel 106 is formed in the inner surface of cavity 104 extending circumferentially around cavity 104 and spaced axially from the upper surface and a second O-ring channel 108 is formed in the inner surface of cavity 104 extending circumferentially around cavity 104 and spaced axially from the lower surface. Further, an O-ring channel 112 is formed in the outer surface of block 102 extending circumferentially around block 102 and spaced axially from the upper surface and a second O-ring channel 114 is formed in the outer surface of block 102 extending circumferentially around block 102 and spaced axially from the lower surface. Also, one or more longitudinally extending passageways or elongated slots 110 are formed to extend through the side of block 102 between the sets of O-ring channels 106/108 and 112/114.

A semipermeable membrane 120, which as explained above preferably includes microporous structure, is wrapped around measurement cavity block 102 and over an O-ring 122 in channel 112 and an O-ring 124 in channel 114. Any lengthwise or other seams are sealed to prevent leakage and O-rings 122 and 124 seal the assembly from the outside environment. While an O-rings and mating channels are illustrated and described for convenience, it will be understood that any suitable sealing mechanism can be employed.

A generally disk shaped sensor mounting plate 130 has a suitable sensor assembly 132 mounted approximately centrally on a lower surface thereof. An O-ring 134 is inserted into O-ring channel 106. Sensor assembly 132 is axially aligned with the upper end of cavity 104 and sensor mounting plate 130 is brought into abutting engagement with the upper end surface of measurement cavity block 102. In this position sensor assembly 132 is sealed against the inner surface of cavity 104 by O-ring 134. A second generally disk shaped sensor mounting plate 140 has a suitable sensor assembly 142 mounted approximately centrally on an upper surface thereof. An O-ring 144 is inserted into O-ring channel 108. Sensor assembly 142 is axially aligned with the lower end of cavity 104 and sensor mounting plate 142 is brought into abutting engagement with the lower end surface of measurement cavity block 102. In this position sensor assembly 142 is sealed against the inner surface of cavity 104 by O-ring 144.

The entire assembly is secured by threading sets of screws 146 through sensor mounting plate 130 into holes 147 in the upper end of measurement cavity block 102 and sets of screws 148 through sensor mounting plate 140 into holes 147 in the lower end of measurement cavity block 102. It should be noted that in place of the O-rings described any other suitable sealing mechanisms and/or combinations thereof can be employed, for example adhesives, gaskets, etc. Also, to prevent stretching and deflection of membrane 120, suitable mechanical supports, such as porous frits, fabrics, or even wire-mesh can be employed to buttress the membrane on either or both sides with due consideration to aspects of seal and integrity.

Sensor assemblies 132 and 142 preferably include a pair of sensors generally designed to operate in cooperation with each other. For example, when the analyte of interest is one that absorbs infrared radiation at specific wavelengths, at least one infrared radiation source (e.g. a semiconductor diode or the like) is positioned in sensor assembly 132 and at least one infrared radiation detector (e.g. a semiconductor photosensor or the like) is positioned in sensor assembly 142. Devices within sensor assemblies 132 and 142 are connected to external circuitry through connections 152 that extend through sensor mounting plates 130 and 140, respectively. It will of course be understood that sensors other than, or in addition to, infrared sensors may be incorporated. Further, while sensors generally designed to operate in cooperation are described it will be understood that one sensor assembly 132/134 may include both radiation generator and radiation sensor and the other assembly 134/132 may include a reflector or other enhancing device.

In operation, when a liquid, represented by arrow 150, flows past (or otherwise comes into contact with) membrane 120, any analytes in the liquid (i.e. a representative quantity) pass through membrane 120, through passageways or elongated slots 110, and into measurement cavity 104. In the infrared example, sensor assembly 132 generates infrared radiation that is received by sensor assembly 142 after passing through any fluid in measurement cavity 104. Thus, in this specific example sensor assembly 142 senses the amount of analyte in cavity 104 and sends an electrical or optical signal through external leads (not shown) coupled to connections 152. By placing a cooperating pair of sensors at opposite ends of cavity 104, sensitivity is improved because absorption by the walls of measurement cavity 104 is minimized.

Figure 5:
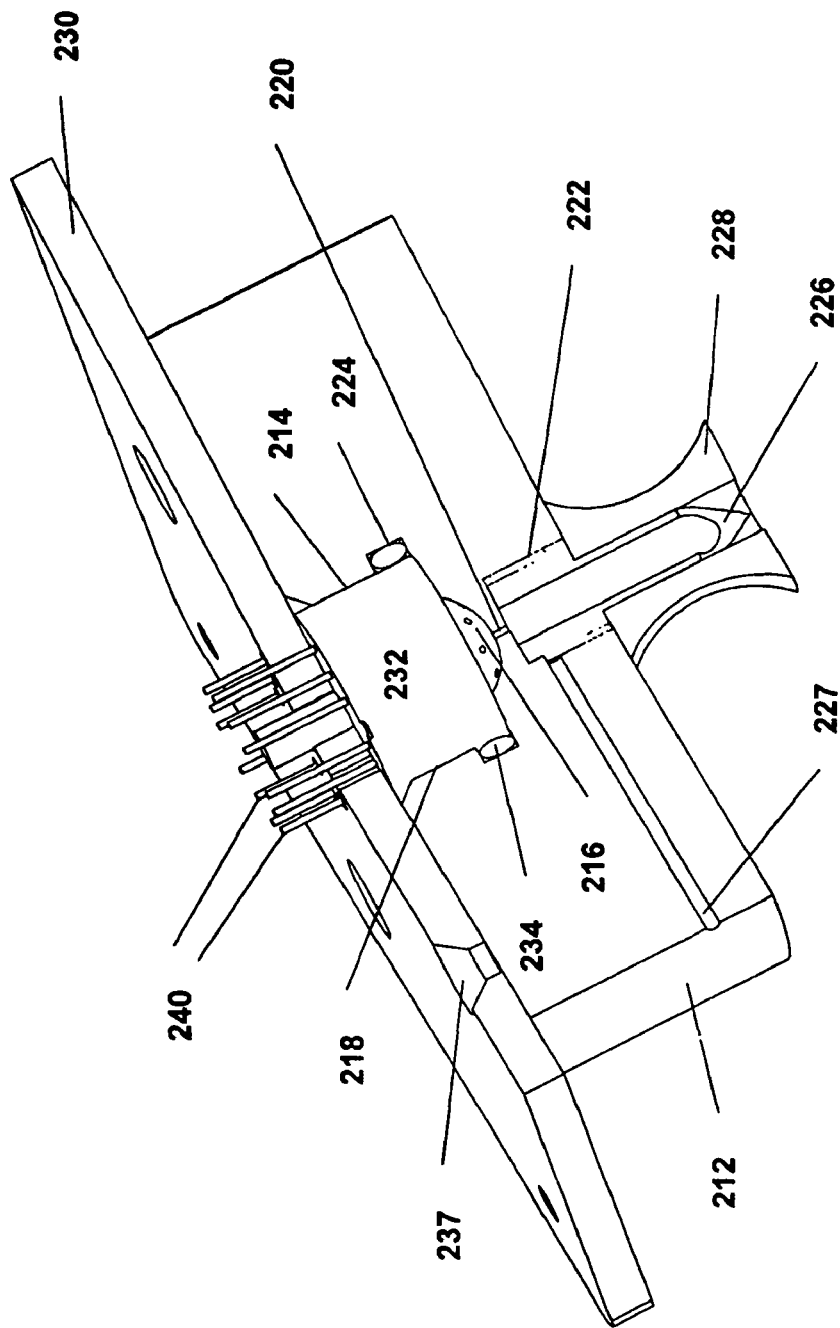
FIG. 5 is a view in perspective, portions thereof cut away, of another embodiment of analyzer apparatus, in accordance with the present invention.

Turning now to FIG. 5, another embodiment of analyzer apparatus, designated 200, is illustrated. Analyzer apparatus 200 is specifically designed to measure compositional gas in, for example, the head space in bottles. In the past, conventional devices and methods only measured the pressure, generally of specific components, within bottles.

Analyzer apparatus 200 includes a measurement cavity block 212, which in this embodiment is generally cylindrical in shape and defines a central cylindrical cavity 214. Cavity 214 has a generally dome shaped upper portion and, as will be explained presently, includes a measurement cavity 216 and a sensor receiving cavity 218. One or more axially extending fluid communication channels or holes 220 extend between the upper end of dome shaped measurement cavity 216 and the inner surface of a needle mounting opening 222 in the surface of block 212. Also, in this embodiment, an O-ring channel 224 extends around the periphery of cavity 214 between measurement cavity 216 and sensor receiving cavity 218.

A detector mounting plate 230 has a suitable sensor assembly 232 mounted on the upper surface thereof. As will become clear from the description below, the various sensor assemblies described herein may contain one or more sensors. Plate 230 is formed to mate with the lower surface of block 212 and sensor assembly 232 is formed in a generally cylindrical shape to fit snuggly within sensor receiving cavity 218. An O-ring 234 is positioned in O-ring channel 224 in cavity 214 and engages the outer surface of sensor assembly 232 to seal measurement cavity 216 from the outside environment. While an O-ring and mating channel are illustrated and described for convenience, it will be understood that any suitable sealing mechanism can be employed to secure and seal sensor assembly 232 to measurement cavity block 212 and, thereby, to seal measurement cavity 216. The entire assembly is secured by using screws (not shown) that insert through holes 237 in detector mounting plate 230 and thread into holes in measurement cavity block 212.

A hollow needle 226, designed specifically to be inserted through the seal, cap, etc. of a bottle containing a liquid to be analyzed is mounted in needle mounting opening 222 by any convenient means. A flexible skirt 228, e.g., rubber, plastic, or the like, is positioned around needle 226 to seal needle 226 with a bottle cap or top and prevent ingress of surrounding atmosphere into the assembly. Further, with needle 226 mounted in opening 222, fluid communication channels or holes 220 conduct gas to be analyzed from needle 226 directly to measurement cavity 216. A bleed line 227 is formed in block 212 in communication with needle mounting opening 222 and may be used in different applications for different purposes. Bleed line 227 may simply be closed to prevent the escape of gas in some applications or may be used for pressurizing measurement cavity 216 with a gas substantially free of the analyte of interest. In other applications, bleed line 227 may connect gas in the bottle being tested from needle 226 to an external pressure gauge or sensor. In yet other applications, bleed line 227 might be used for in-line processing by applying a pressure to the liquid being analyzed. For example, when one is interested in measuring the analyte levels in a liquid flowing in a pipe, a sampling tube may be connected to the analyzer cavity directly to the needle mounting port 222. In case the pressure in the pipe is excessive, liquid may penetrate the measurement cavity 216. To prevent such an occurrence, one may apply an equal, opposing pressure in the measurement cavity by pressurizing with a gas that is substantially free from the analyte by supplying it through the bleed line 227. In a still further application, bleed line 227 might be attached to a valve to release pressure in needle 226 after testing has been completed.

Figure 6:
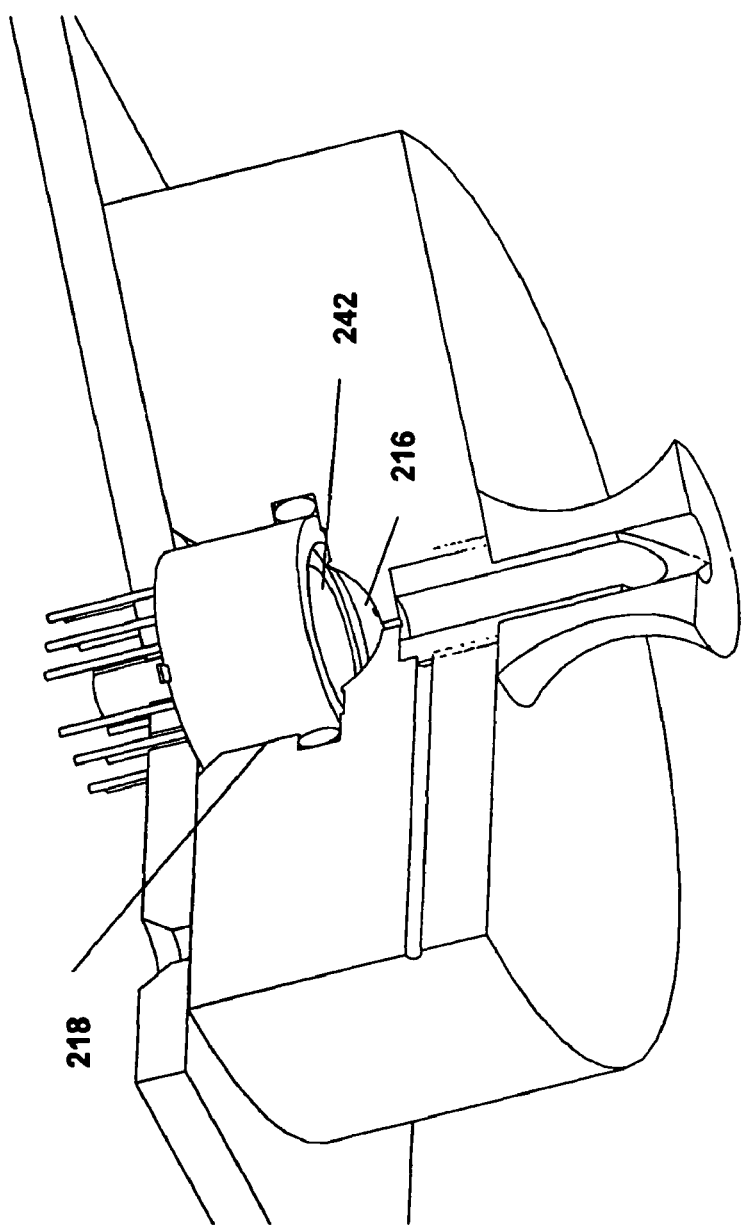
FIG. 6 is a view in perspective, portions thereof cut away, of the analyzer apparatus of FIG. 5 with a modification.

Sensor assembly 232 includes one or more suitable sensors selected for the specific analyte or analytes being measured and generates electrical or optical signals in response to the amounts of analyte sensed in measurement cavity 216. Sensor electrical or optical connections 240 extend from sensor assembly 232 through detector mounting plate 230 to provide external connections. As illustrated in FIG. 6, when optical sensors are used a window 242 may be included in one of measurement cavity 216 and sensor receiving cavity 218 or in-between the cavities.

Thus, in operation, needle 226 is inserted through the cap or other seal on a bottle of liquid to be tested. Gas contained within the bottle that emanated from the liquid within the bottle flows through hollow needle 226, through fluid communication channels or holes 220, and directly into measurement cavity 216. Suitable sensors carried by sensor assembly 232 sense one or more selected analytes and provide analysis signals at sensor electrical or optical connections 240.

Figure 7:
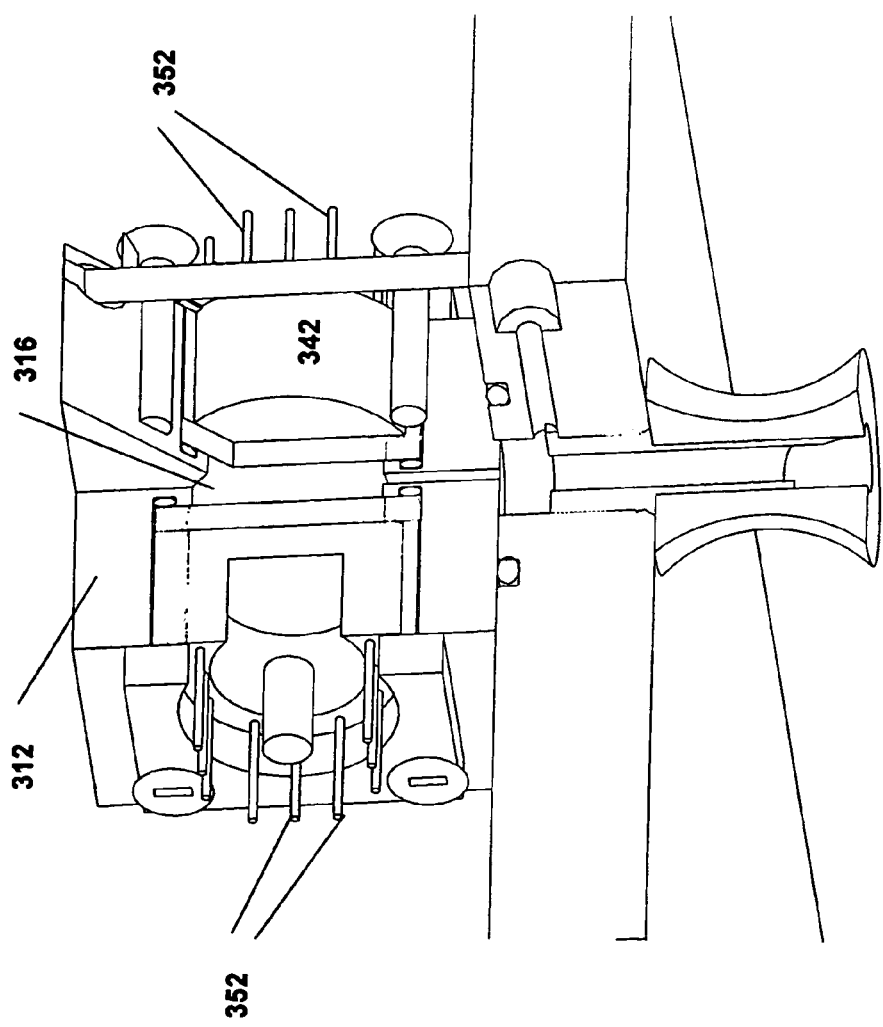
FIG. 7 is a view in perspective, portions thereof cut away, of another embodiment of analyzer apparatus, in accordance with the present invention.

Turning to FIG. 7, an analyzer assembly, designated 300, is illustrated. Analyzer assembly 300 is basically similar to analyzer assembly 200 except that a measurement cavity block 312 defines a central measurement cavity 316 situated between two sensor assemblies 332 and 342 that are mounted in directly opposed relationship on opposite sides of cavity 316. Sensor assemblies 332 and 342 include a pair of sensors generally designed to operate in cooperation with each other. For example, when the analyte of interest is one that absorbs infrared radiation at specific wavelengths, at least one infrared radiation source (e.g. a semiconductor diode or the like) is positioned in sensor assembly 332 and at least one infrared radiation detector (e.g. a semiconductor photosensor or the like) is positioned in sensor assembly 342. Devices within sensor assemblies 332 and 342 are connected to external circuitry through connections 352. It will of course be understood that sensors other than, or in addition to, infrared sensors may be incorporated. Further, while sensors generally designed to operate in cooperation are described it will be understood that one sensor assembly 332/334 may include both radiation generator and radiation sensor and the other assembly 334/332 may include a reflector or other enhancing device.

In any of the embodiments described above, it should be understood that once measurements of the analyte in the measurement chamber are completed several different methods of determining the amount of analyte in the liquid sample can be used. Based on the thermodynamic vapor-liquid equilibrium relationships, an estimate of the corresponding concentration of analyte dissolved in the liquid by measuring the amounts of analyte in the measurement cavity can be performed or, alternately, the analyte amount measured in the measurement cavity can itself be directly used as a measure of its corresponding concentration in the liquid.

In some applications, measuring the total pressure in the measurement cavity might be sufficient to estimate the analyte amounts (concentration) in the liquid. However, the total pressure may be a poor indicator of the analyte amount when there are multiple volatile substances, or when the liquid itself has a significant vapor pressure. For example, when measuring the amount of dissolved carbon dioxide when there is a finite amount of dissolved oxygen and nitrogen from air, using total pressure measurements cause a significant overestimation of the dissolved carbon dioxide concentration. One solution to this problem is to provide a detector that is sensitive only to the analyte of interest. Special analyte detectors and/or membranes will provide an accurate determination of the analyte quantities without interferences from other substances. Suitable detectors may vary with the specific analyte of interest. For example, when the analytes of interest include carbon dioxide or certain volatile organic compounds, a detector might assess the absorption of infrared radiation at the appropriate wavelengths. If measuring the concentration of electrochemically oxidizable or reducible analytes, an electrochemical detector might be more appropriate. If the analyte contains sulfur atoms, a sulfur chemiluminescence detector might be appropriate. If the analyte contains halogen groups, an electron-capture-efficiency detector might be more appropriate. In each application it is preferred to use an analyte sensor that is specific to the type of analyte being sensed. Also, in some applications a membrane can be designed to pass an analyte of interest while blocking other prevalent analytes.

Thus, new and improved analyzer apparatus for measuring amounts of dissolved volatile substances in a liquid are disclosed. In one type the novel analyzer apparatus includes a semipermeable membrane with microporous structure to provide extremely high diffusion rates and a membrane that can be specifically developed for a wide variety of analytes. Since high diffusion rates allow rapid equilibrium between the measurement cavity and the liquid sample, they minimize response time, which also minimizes the risk of condensation of vapor within the measurement cavity. It is also preferable to minimize response time because the absorption of the analyte by the membrane material is minimized. In another type, no membrane is included but the apparatus is designed to communicate directly with sealed bottles and the like. Also, the novel construction in either type greatly reduces the size of the measurement cavity and the analyte inlet to further minimize response time. In addition to the novel apparatus, a new and improved method for measuring the amounts of dissolved volatile substances in a liquid is disclosed.

Various changes and modifications to the embodiment herein chosen for purposes of illustration will readily occur to those skilled in the art. To the extent that such modifications and variations do not depart from the spirit of the invention, they are intended to be included within the scope thereof which is assessed only by a fair interpretation of the following claims.

Having fully described the invention in such clear and concise terms as to enable those skilled in the art to understand and practice the same, the invention claimed is:

1. Analyzer apparatus for measuring amounts of at least one specific analyte dissolved in a liquid external to the analyzer apparatus comprising:
   a measurement cavity block defining a measurement cavity and an analyte inlet, the analyte inlet having one side in communication with the measurement cavity and an opposed side positionable to communicate with the specific analyte dissolved in the liquid;
   an analyte sensor and sensor assembly, the analyte sensor selected to sense the at least one specific analyte and sensitive only to the at least one specific analyte to provide a determination of analyte amount without interference from other substances, the analyte sensor assembly including an infrared radiator and infrared sensor pair;
   the analyte sensor assembly sealingly affixed to the block with the analyte sensor in communication with the measurement cavity, the sensor assembly sealing the measurement cavity from environment outside the measurement cavity with the infrared radiator mounted to radiate infrared through the measurement cavity to the infrared sensor; and
   a semipermeable membrane affixed to the measurement cavity block over the analyte inlet and constructed to allow the at least one specific analyte to pass through the membrane into the measurement cavity while restricting the liquid from flowing into the cavity, the measurement cavity being sealed from environment outside the measurement cavity except for analyte entering the measurement cavity through the semipermeable membrane, whereby the analyte sensor senses only the at least one specific analyte without the introduction of any other substance.

2. Analyzer apparatus for measuring amounts of at least one specific analyte dissolved in a liquid as claimed in claim 1 wherein the semipermeable membrane includes a quick response time membrane with microporous structure.

3. Analyzer apparatus for measuring amounts of at least one specific analyte dissolved in a liquid as claimed in claim 1 wherein the analyte inlet and the measurement cavity have a size reduced to minimize response time.

4. Analyzer apparatus for measuring amounts of at least one specific analyte dissolved in a liquid as claimed in claim 1 wherein the analyte sensor assembly operates by measuring at least one property of the at least one specific analyte, the properties including electromagnetic radiation absorption, thermal Conductivity, oxidation, reduction, and luminescence.

5. Analyzer apparatus for measuring amounts of at least one specific analyte dissolved in a liquid as claimed in claim 1 wherein the measurement cavity block defines a single opening into the measurement cavity and a single sensor mounting plate having the analyte sensor assembly mounted thereon is affixed to the block with the analyte sensor assembly in communication with the measurement cavity, and the single sensor mounting plate sealing the measurement cavity from environment outside the measurement cavity.

6. Analyzer apparatus for measuring amounts of at least one specific analyte dissolved in a liquid as claimed in claim 1 wherein the measurement cavity block defines two spaced apart openings into the measurement cavity and two sensor mounting plates with the analyte sensor assembly mounted thereon are affixed to the block with the analyte sensor assembly in communication with the measurement cavity, and the two sensor mounting plates sealing the measurement cavity from environment outside the measurement cavity.

7. Analyzer apparatus for measuring amounts of at least one specific analyte dissolved in a liquid as claimed in claim 1 wherein the semipermeable membrane is formed using a material including one of silicone, polyolefin, polyamide, polysulfone, and polytetrafluoroethylene, polyvinyledene difluoride.

8. Analyzer apparatus for measuring amounts of a specific analyte dissolved in a liquid external to the analyzer apparatus comprising:
  a measurement cavity block defining a measurement cavity and an analyte inlet, the analyte inlet having one side in communication with the measurement cavity and an opposed side positionable to communicate with the specific analyte dissolved in the liquid, the analyte inlet and the measurement cavity having a size reduced to minimize response time;
  an analyte sensor assembly selected to sense the specific analyte and sensitive only to the specific analyte to provide a determination of analyte amount without interference from other substances, the analyte sensor assembly including an infrared radiator and infrared sensor pair with the infrared radiator mounted to radiate infrared through the measurement cavity to the infrared sensor;
  at least one sensor mounting plate having the analyte sensor assembly mounted thereon, the at least one sensor mounting plate being affixed to the block with the analyte sensor assembly in communication with the measurement cavity, and the at least one sensor mounting plate and sensor assembly sealing the measurement cavity from environment outside the measurement cavity; and
  a semipermeable membrane including microporous structure affixed to the measurement cavity block over the analyte inlet and constructed to allow the specific analyte to pass through the membrane into the measurement cavity while restricting the liquid from flowing into the cavity, the measurement cavity being sealed from environment outside the measurement cavity except for analyte entering the measurement cavity through the semipermeable membrane, whereby the analyte sensor assembly senses only the specific analyte without the introduction of any other substance.

9. Analyzer apparatus for measuring amounts of a specific analyte dissolved in a liquid as claimed in claim 8 wherein the measurement cavity block defines a single opening into the measurement cavity and a single sensor mounting plate having the analyte sensor assembly mounted thereon is affixed to the block with the analyte sensor assembly in communication with the measurement cavity, and the single sensor mounting plate sealing the measurement cavity from environment outside the measurement cavity.

10. Analyzer apparatus for measuring amounts of a specific analyte dissolved in a liquid as claimed in claim 8 wherein the measurement cavity block defines two spaced apart openings into the measurement cavity and two sensor mounting plates with the analyte sensor assembly mounted thereon are affixed to the block with the analyte sensor assembly in communication with the measurement cavity, and the two sensor mounting plates sealing the measurement cavity from environment outside the measurement cavity.

11. Analyzer apparatus for measuring amounts of a specific analyte dissolved in a liquid as claimed in claim 10 wherein the analyte sensor assembly includes an infrared radiator and infrared sensor pair with the infrared radiator mounted on one of the two sensor mounting plates and the infrared sensor mounted on the other of the two sensor mounting plates.

12. Analyzer apparatus for measuring amounts of a specific analyte dissolved in a liquid as claimed in claim 8 wherein the semipermeable membrane is formed using a material including one of silicone, polyolefin, polyamide, polysulfone, and polytetrafluoroethylene, polyvinyledene difluoride.

13. Analyzer apparatus for measuring amounts of at least one specific analyte dissolved in a liquid external to the analyzer apparatus comprising:
  a measurement cavity block defining a measurement cavity and an analyte inlet, the analyte inlet having one side in communication with the measurement cavity and an opposed side positionable to communicate with the specific analyte dissolved in the liquid, wherein the measurement cavity block defines two spaced apart openings into the measurement cavity and two sensor mounting plates are affixed to the block over the two spaced apart openings and sealing the measurement cavity from environment outside the measurement cavity;
  an analyte sensor and sensor assembly, the analyte sensor selected to sense the at least one specific analyte and sensitive only to the at least one specific analyte to provide a determination of analyte amount without interference from other substances, the analyte sensor assembly includes an infrared radiator and infrared sensor pair with the infrared radiator mounted on one of the two sensor mounting plates and the infrared sensor mounted on the other of the two sensor mounting plates; and
  a semipermeable membrane affixed to the measurement cavity block over the analyte inlet and constructed to allow the at least one specific analyte to pass through the membrane into the measurement cavity while restricting the liquid from flowing into the cavity, the measurement cavity being sealed from environment outside the measurement cavity except for analyte entering the measurement cavity through the semipermeable membrane, whereby the analyte sensor senses only the at least one specific analyte without the introduction of any other substance.

14. Analyzer apparatus for measuring amounts of a specific analyte dissolved in a liquid external to the analyzer apparatus comprising:
  a measurement cavity block defining a measurement cavity and an analyte inlet, the analyte inlet having one side in communication with the measurement cavity and an opposed side positionable to communicate with the specific analyte dissolved in the liquid, the analyte inlet and the measurement cavity having a size reduced to minimize response time, wherein the measurement cavity block defines two spaced apart openings into the measurement cavity and two sensor mounting plates affixed to the block over the two spaced apart openings and sealing the measurement cavity from environment outside the measurement cavity;
  an analyte sensor assembly selected to sense the specific analyte and sensitive only to the specific analyte to provide a determination of analyte amount without interference from other substances, the analyte sensor assembly including an infrared radiator and infrared sensor pair with the infrared radiator mounted on one of the two sensor mounting plates and the infrared sensor mounted on the other of the two sensor mounting plates; and a semipermeable membrane including microporous structure affixed to the measurement cavity block over the analyte inlet and constructed to allow the specific analyte to pass through the membrane into the measurement cavity while restricting the liquid from flowing into the cavity, the measurement cavity being sealed from environment outside the measurement cavity except for analyte entering the measurement cavity through the semipermeable membrane, whereby the analyte sensor assembly senses only the specific analyte without the introduction of any other substance.

\* \* \* \* \*